United States Patent
Cooper

[19]

[11] Patent Number: 5,825,458
[45] Date of Patent: Oct. 20, 1998

[54] PERSONAL BINOCULAR TRAINER

[76] Inventor: Clifford Warren Cooper, P. O. Box 5125, Hyattsville, Md. 20782-0125

[21] Appl. No.: 397,637

[22] Filed: Mar. 2, 1995

[51] Int. Cl.[6] .................................................. A61B 3/00
[52] U.S. Cl. .................................... 351/203; 351/200
[58] Field of Search ............................ 351/203, 200, 351/218, 245, 246; 128/76.5

[56] References Cited

U.S. PATENT DOCUMENTS

| | | | |
|---|---|---|---|
| 0,871,103 | 11/1907 | Bridge | 351/203 |
| 1,702,700 | 5/1929 | Martin | 128/76.5 |
| 2,102,490 | 12/1937 | Simpkins | 351/203 |
| 2,263,190 | 11/1941 | Quinan | 128/76.5 |
| 3,875,934 | 4/1975 | Sadanaga | 351/203 |
| 4,035,066 | 7/1977 | Slomski | 351/203 |
| 4,260,266 | 4/1981 | Ghahramani | 351/203 |
| 4,464,027 | 8/1984 | Cooper | 351/203 |
| 4,506,963 | 3/1985 | Cooper | 351/203 |

*Primary Examiner*—Hung X. Dang

[57] ABSTRACT

A device for training the binocular function of the human visual system for optimal performance. The device is comprised of a horizontal shaft, with a handle substantially in the center of it. It has two stationary vertical posts. One post is affixed to each end of the shaft. The posts are aligned in a spaced apart relationship in the same vertical plane. When combined the elements of this device induce physiological diplopia and enable it to be used dynamically as visual biofeedback during training. The visual biofeedback is informative because it provides the user with proof that their visual system is focused binocularly. Training systematically and methodically recalibrates the musculature of the human visual system, thereby enhancing its performance. Use of the personal Binocular Trainer also increases the user's attention span and comprehension.

3 Claims, 2 Drawing Sheets

PERSONAL BINOCULAR TRAINER

BACKGROUND—FIELD OF INVENTION

This invention relates to the fields of vision therapy, orthoptics, optometry, ophthalmology, sports vision and education. This invention can be used to test, exercise, recalibrate and otherwise improve the musculature of the human visual system. It specifically provides a means to correct, muscle imbalances, convergence insufficiency and eyestrain.

BACKGROUND—DESCRIPTION OF THE PRIOR ART

My review of the prior art revealed numerous inventions that were designed to evaluate the status of an individual's visual system. Most of these devices were invented to help optometrists, ophthalmologists and orthoptists ascertain the status of an individual's visual system in terms of binocular coordination.

Bridge's "Optical Instrument," 871,103 (1907) was designed to test and treat the human visual system. To use Bridge's '103 the user first adjusts the apparatus to achieve eye-to-aperture (3) correspondence by using knob (14). After achieving eye-to-aperture correspondence the technician reads the users interocular distance of the scale on the side of the beam. When the user adjusts knob (14) for eye-to-aperture correspondence he or she simultaneously adjusts the distance between the devices prismatic lenses. The individual's eyes are then tested one at a time, this is accomplished by occluding one of the apertures during testing. A reading card with test characters or other symbolic information is placed in the slidable card holder (6) which is mounted on beam/scale (5) at a point on the beam/scale where it could be seen clearly by someone of normal vision. At this place on the beam the scale reads No. 0 (for zero diopter). If the individual can not see the test characters at this distance, the card is slowly slid along the beam/scale toward the user until they can see it clearly. The technician then reads the scale to determine the number of the corrective lens that is necessary to correct the individual's vision in that eye. The user then repeats the same test for the opposite eye.

The eyes are exercised by Bridge's '103 by viewing the cards (6) while the operator manipulates the prismatic lenses (11) to and away from the user thereby exercising the accommodate reflex, the reflex which is necessary for the user to keep the information on the card (6) in focus while is moving.

Bridge's '103 is interesting, and appears to have been invented for use by individuals engaged in the practice of optometry or vision therapy. Bridge's '103 is truly an optical instrument in so far as it can be used to test acuity and for other optical problems such as astigmatism. One disadvantage of this invention is its complexity. Another disadvantage is the fact that it requires frequent adjustment. It had limited utility when it was invented, in so far as it was probably designed for use by people who prescribed ground glass lenses, such as optometrists. Bridge's '103 appears to be the progenitor of the visual testing apparatus currently used by most motor vehicle administrations to screen applicant's vision.

Martin's "Eye Exercising Apparatus," 1,702,700 (1929) was designed to train the medial rectus and inferior oblique rectus muscles of the visual system to enhance convergence. When using the device the user focuses his eyes on the fixation object which is moving toward them. At the end of its travel toward the user, the movable fixation object travels downward and out of sight. The user then refocuses his visual system on the next fixation object and repeats the process. One of the obvious disadvantages of this design is its complexity, there are simply too many fixation objects. After you track the first fixation object through its travel and it disappears the user must refocus his visual system on the next movable fixation object, and the process is repeated. A second disadvantage is training occurs in only one direction. The medial rectus muscles and the lateral rectus muscles operate in opposition to each other. This invention may actually have caused a muscle imbalance if favor the medial rectus muscles, because it would tended to make them stronger than their counterparts, the lateral rectus muscles.

Simpkins' "Means for Investigating, Correcting, and Developing the Power of Human Vision," 2,102,490 (1937) was designed to improve the acuity of the visual system by selectively exercising the certain muscle groups thereby developing the power of human vision. Simpkins' '490 teaches us that if there is a weakness in a particular muscle that performs a particular function of an eye, and weakness of vision results therefrom, then one can exercise that particular muscle or group of muscles and remove such resulting weakness of vision. A user of Simpkins device moves a sliding/traversable member ($f^o$) along the mount (c) in a to and from motion, (like that used when playing the trombone), while focusing their eyes binocularly on a focal disc (k) with a "bull's eye" painted on it (concentric circles), this exercise was conceived of for the purpose of overcoming problems associated with weak or defective medial and lateral rectus muscles. Simpkins' '490 also provides for exercising the muscles of the eyes in a circular pattern through the use of what he describes an adaptor/turntable (FIG. 6 Simpkins '490). The adaptor/turntable is installed by inserting vertical bearing ($i^2$) into the round bushing provided by the sliding/traversable member ($f^o$) described above.

To enable the turntable function, the user would slide bar (i) to the right and insert a focal disc into socket ($i^4$) and rotate the adaptor in a circular pattern or an angular distance about the vertical axis of ($i^2$)in either direction left or right while focusing their eyes on the focal disc.

To enable the adaptor function, the user would leave the slide bar (i) in the position pictured in FIG. 6 of Simpkins' '490 and insert two focal discs, one in each socket ($i^4$) and move the sliding/traversable member along the mount c in a to and fro motion while maintaining stereo-monocular focus with the visual axes parallel, i.e. each eye focusing on the bull's eye of focal disc (k) on the same side of the mount as the respective eye.

Simpkins' '490 is the only patented device that I reviewed which provides for exercise of a stereo-monocular form of vision. One of the obvious disadvantages of this invention is its complexity. It also lacks a means for the user to ascertain the status of their training, such as visual feedback, other than having an image in focus or out of focus.

Quinan's "Sight Rectifier," 2,263,190 (1940) was designed to train the medial and lateral rectus muscles, inferior and superior rectus muscles, and the inferior and superior oblique muscles. His invention is based on the method of the late Horatio Bates. When using this invention the user focuses his eyes on movable stimulus which is selected to exercise the muscles in a particular pattern. For example, in a circle, ellipse, or along a diagonal axis. Quinan invented the "Sight Rectifier," for the purpose of restoring the spherical shape of the human eye.

The Sight Rectifier was invented to effect a physiological adjustment of the optics of the visual system by making the extrinsic muscles stronger so that they would not have to work so hard to move the eyes. The muscles then could relax and allow the eye to assume its normal shape and refraction.

One of the disadvantages of Quinan's invention is its too complex. A second problem with the "Sight Rectifier," the exercise it provides is not symmetrical about the medial plane that bisects the human visual system. A third problem is it was bulky, required frequent adjustment which made it awkward to use. A fourth problem is that it does not provide any means for the user to determine if they are using it correctly.

Sadanaga's "Device for Training Ocular Muscles," 3,875,934 was designed to relieve pseudo-myopia, eyestrain, and train the ocular muscles. The user uses this device to exercise the visual system by focusing on targets moving in a selected manner through prisms and lenses. One of the obvious disadvantages of this invention is its complexity. It also lacks a means for the user to ascertain the status of their training other than whether the image that they have is in or out of focus.

Slomski's "Apparatus for Testing Stereoscopic Vision," 4,035,066 (1977) was designed to test and individuals spatial (depth) perception. The user of this device simply looked into the apparatus and used it to align three stimulus objects on a line perpendicular to the user's line of sight. It was not designed to provide exercise which would improve an individual's vision or spatial perception.

Ghahramani's "Eye Depth Perception Testing Apparatus," 4,260,266 (1981) was designed to test an individuals depth perception. The user of this device simply looked into the apparatus and tried to align two stimulus objects on a line perpendicular to the user's line of sight. It was not designed to provide exercise which would improve an individuals vision or depth perception.

My original "Binocular Trainer," 4,464,027 (1984), 4,506,936 (1985) was invented specifically for the purpose of diagnosing then systematically and methodically improving the user's binocular vision. This device utilizes two stationary posts which have a spaced apart relationship and one movable post which the user moves from a position directly above the first stationary post to a position directly above the second stationary post. The spaced apart relationship of the first and second stationary posts creates a three dimensional field, consisting of height (x), width (y), and depth (z). The movable stimulus adds the dimension of time (t). When the user bi-fixates his eyes on the movable stimulus, the stationary posts induce physiological diplopia. Physiological diplopia occurs whenever an individuals eyes are focused binocularly on a particular image plane. All of the visual information on every image plane bisected by the line of sight is out of focus and appears double and symmetrical. So when the user has his eyes bi-fixated on the movable stimulus while it is directly over the first stationary post, the second stationary post appears double and symmetrical. When the user has his eyes bi-fixated on the movable stimulus and it is approximately half of the way between the first stationary post and the second stationary post, the first and second stationary posts both appear double. For every position of the movable stimulus relative to the stationary stimulus there exists corresponding symmetrical visual biofeedback. The double images or visual biofeedback provide proof to the user that his visual system is focused binocularly. In order for the user to benefit from the use of the original "Binocular Trainer," the user must keep their visual system focused binocularly and remain cognizant of the presence of the symmetrical visual biofeedback, without looking directly at it.

The major disadvantages of the original "Binocular Trainer," are its expense and lack of portability. It was designed to be used by optometric technicians, medical technicians, and educators in the clinical or educational setting.

BACKGROUND—OF THE PROBLEM

The purpose of my invention is to provide a simple, efficient, and economical device that can be used to systematically and methodically recalibrate the human visual system, thereby eliminating subtle physiological problems such as convergence insufficiency, muscle imbalances, poor oculomotor control, eyestrain, and other physiological problems that can and do interfere with the binocular functioning of an individual's visual system.

Historically, diagnosis and treatment have both been a problem. The fact that most people are able to focus their visual systems binocularly for brief periods of time, for example, long enough to pass a stereo-graphic four dot test, merely confounds the problem. The static nature of the stereographic four dot test is a weakness of the standard optometric examination. The problem is that individuals who pass the test may be unable to maintain binocular focus for extended periods of time. There are numerous physiological conditions that are extremely subtle that can and do interfere with the binocular functioning of an individual's visual system. Reading is an activity that requires an individual to sustain binocular focus for an extended period of time. That is why I have decided to address it specifically in this document.

OBJECTS AND ADVANTAGES

One of the principal objects of this invention is to provide an improved device for exercising the extrinsic muscles of the human visual system.

Another principal object of the invention is to provide a novel and improved means for selectively relaxing and contracting the muscles of the human visual system.

Another principal object of the invention is to provide a novel and improved means for the systematic and methodical elimination of physiological obstacles that interfere with an individual's ability to read proficiently and otherwise develop his or her intelligence. Intelligence in the context of this document relates to the ability to gather, organize, assimilate, and use information.

Still another principal object of the invention is to provide an improved device for exercising and strengthening the extrinsic musculature of the visual system, thereby reducing the amount of effort required to initiate and sustain binocular focus.

Another object of the invention is to provide a novel and improved device for systematically and methodically recalibrating the extrinsic and intrinsic musculature of the human visual system.

A further object of the invention is to provide a novel and improved device for training the coordination of the extrinsic and intrinsic muscles of visual system for greater ease and efficiency in binocular vision.

Another object of the invention is to provide an improved device for exercising the accommodative functions of the eyes and increasing fusional capacity of the visual system, thereby increasing the amount of time the visual system can be focused binocularly without experiencing eyestrain or fatigue.

Still another object is to provide an apparatus and method to bring about improved coordination between accommodation and convergence for greater efficiency in the performance of the eyes in binocular vision.

Another object is to provide a novel simple and improved device for exercising the eyes to bring about increased amplitude of accommodation.

Another object of the invention is to provide an improved device for the purpose of systematically increasing one's attention span.

Another object of the invention is to provide an improved device for the purpose of systematically and methodically increasing one's comprehension.

A further object of the present invention is to provide a novel and improved device to facilitate the post-operative reconditioning of the musculature of the visual system of medical patients who have had interocular implants or other surgical procedures which may have stretched or otherwise traumatized the intrinsic or extrinsic eye muscles.

A further object is to provide a very simple, inexpensive, and efficient device capable of being used with minimum supervision, to "maintain" the coordination of the intrinsic and extrinsic musculature of the human visual system in accordance with the main purpose of my invention.

Accordingly, several of the advantages of the personal Binocular Trainer are: It is extremely portable. It can be quickly disassembled and placed in a carrying case or backpack and taken to the office, to a park, the beach, or the mountains. It can be reassembled and ready to use in minutes. It can be used in practically any orientation. You can use it while you're laying down. It can be used by people who are right or left handed. It costs less to manufacture than the original Binocular Trainer. It doesn't require any moving parts.

Further objects and advantages of my invention will become apparent from a consideration of the drawings and ensuing description and it will be apparent that many modifications may be made in the details of manufacture, arrangement of components, absolute and relative dimensions, the method of manufacture, and the method of use described without departing from the scope and spirit of the invention as described in the appended claims.

SUMMARY OF THE INVENTION

The personal Binocular Trainer is a hand held device that was designed to test, exercise, recalibrate, and maintain the musculature of the human visual system. The net effect of this training is improved binocular vision, enhanced visual attention, improved comprehension, preservation of accommodative flexibility, and the elimination of attendant problems such as poor comprehension and eye strain.

The personal Binocular Trainer is based on three operative concepts, physiological diplopia, Hering's Law of Equal and Symmetrical Eye Movements, and the notion of musculature plasticity.

1. Physiological diplopia occurs whenever an individuals eyes are focused binocularly on a particular image plane, all of the visual information on every image plane bisected by the line of sight is out of focus and appears double and symmetrical. It is best exemplified using vertical stimuli.
2. Hering's Law of Equal and Symmetrical Eye Movements was articulated by Ewald Hering in 1860's, it states, in so many words, that whenever one eye moves, the opposite eye moves simultaneously in the same or opposite direction and for an equal distance.
3. Musculature plasticity is the fact that all muscles can and do change as a result of exercise.

These three concepts are integrated into the operation of the personal Binocular Trainer. The personal Binocular Trainer induces physiological diplopia and so that it can be used dynamically when recalibrating the user's visual system. If the visual biofeedback is symmetrical and it stays symmetrical, while the individual exercises his visual system, then the individual's eyes are focused binocularly and are functioning in accordance with Hering's Law of Equal and Symmetrical Eye Movements. If, however, the individual's visual experience becomes asymmetrical or intermittent (it flickers) while the visual system is being exercised it indicates that the individuals visual system is not functioning in accordance with Hering's law i.e., the movements of the eyes are not equal and symmetrical and the user needs to exert more influence on their visual system. In some cases the individual's visual system will simply focus on the first post and jump to the second post, or average the distance between the posts. The object of the training is to develop such control and ease of focus that the individual may focus his or her eyes on any of the image planes between the posts in either direction to or fro.

In either case the findings are informative, as they indicate the absence or the presence of a problem, such as a muscle imbalance, convergence insufficiency, that can and will interfere with binocular vision.

The use of the Binocular Trainer strengthens and systematically recalibrates the eye muscles thereby eliminating muscle imbalances, physiology based focusing deficits, eyestrain, fatigue, enhances visual attention and reduces the amount of effort required to initiate and sustain binocular focus.

Visual attention is a zero-sum process, the more physiological effort that is required to keep the visual system in focus the less physiological effort that individual has at their disposal to interpret the semantic meaning of what has been read. Inversely, if you reduce the amount of physiological effort that is expended to keep the visual system in focus, the more physiological effort you have available to interpret the meaning of what was read (comprehension).

The term attention-span, literally, refers to ones ability to focus the eye-brain complex for some span of time. By reducing the amount of physiological effort required to focus the visual system, the personal Binocular Trainer, provides a means whereby an individual can increase the duration of his or her attention-span.

DESCRIPTION OF THE INVENTION

Figure 1:
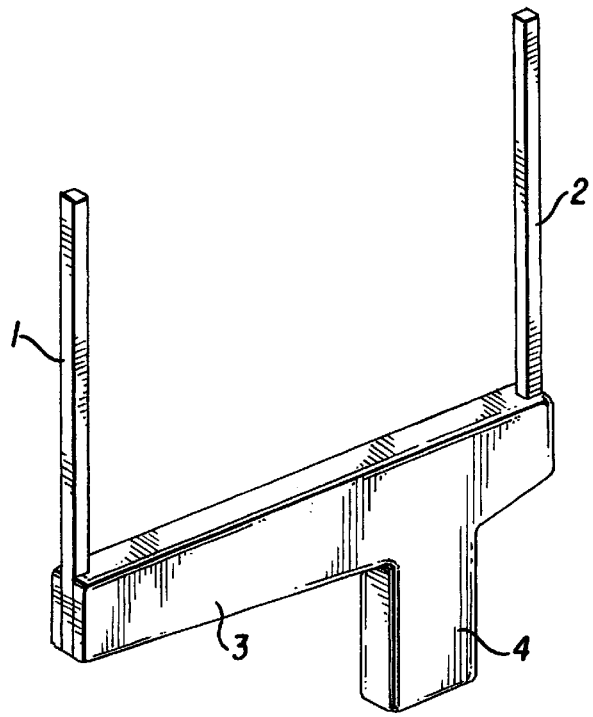
FIG. 1 is a perspective view of the personal Binocular Trainer
Figure 2:
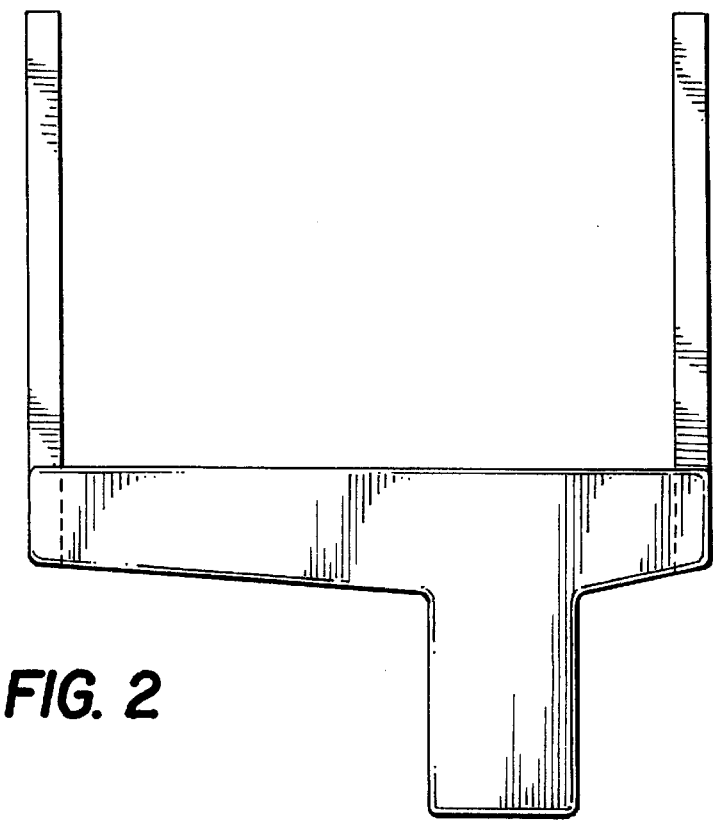
FIG. 2 is a side elevation of the personal Binocular Trainer
Figure 3A:
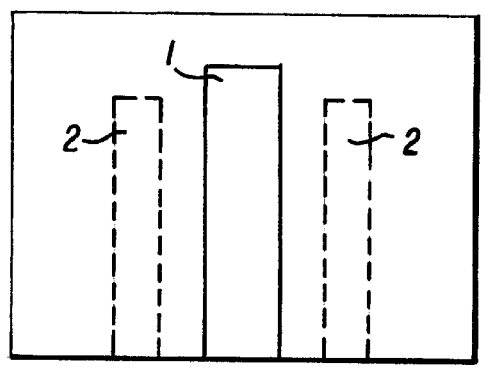
FIG. 3a is a two dimensional representation of the visual image when the user is focusing his eyes on the first post
Figure 3B:
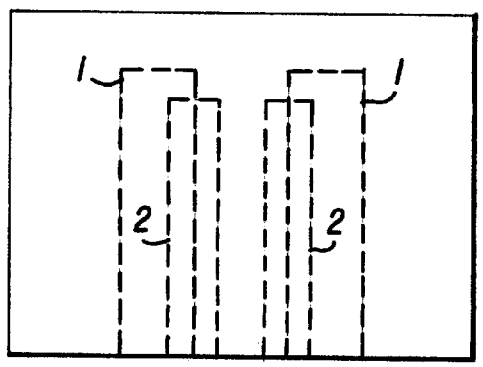
FIG. 3b is a two dimensional representation of the visual image when the user is focusing his eyes halfway between the first and second posts
Figure 3C:
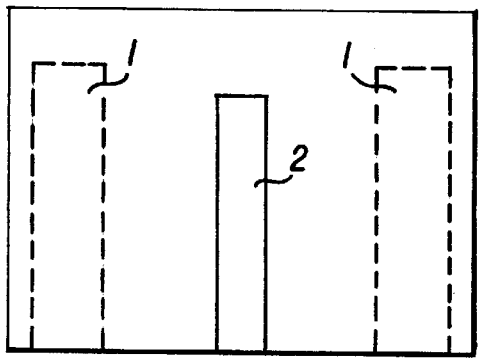
FIG. 3c is a two dimensional representation of the visual image when the user is focusing his eyes on the second post.

The personal Binocular Trainer FIG. 1, consists of a horizontal shaft (3) with a handle substantially in the center of it (4). It has two stationary vertical posts (1) and (2). One post is affixed to each end of the beam. The posts (1) and (2) are aligned in a spaced apart relationship in a vertical plane.

The invention has been described in the context of schematic and representative embodiments. Many variations, substitutions and modifications can be made to the described device, including the absolute or relative dimensions of the parts, materials used, pigments, patterns, method of manufacture, and the like without departing from the spirit and the scope of the invention as described in the appended claim.

DESCRIPTION OF THE PREFERRED EMBODIMENTS

The posts (1) and (2) may be of different colors, and/or may have unique and/or distinctive patterns, and/or attention getting symbols on them to add to the information contained in the visual biofeedback that they generate or to make them more readily perceptible.

The personal Binocular Trainer could be adapted for use in the dark by various means. The posts (1) and (2) may be self illuminating through the incorporation of LED'S (light emitting diodes) luminescent pigmentation, reflective media, the use fiber optics or any combination of the above means or any other suitable means. The illumination of the posts (1) and (2) will increase the utility of the personal Binocular Trainer by allowing it to be used in dark environments with the dark adapted eye.

The personal Binocular Trainer could be adapted to be supported by a stand for hand free operation or display.

The personal Binocular Trainer could be manufactured in a way that would permit the linear distance between the stationary posts to be adjusted.

OPERATION OF THE INVENTION

The vertical plane of the stationary posts is aligned with the vertical plane projecting from through the center of the user which bisects the human visual system. The user holds the personal binocular trainer, with one hand, in the plane described above. The user positions the index finger of the other hand directly over the first stationary post. While keeping their visual system focused on their finger, they unconsciously observe symmetrical visual biofeedback without refocusing their visual system on it. The fact that the visual biofeedback is symmetrical is proof that their visual system is focused binocularly. The user then gradually moves their finger from a position immediately above the first stationary post to a position immediately above the second stationary post while observing the visual biofeedback (without refocusing on it directly). The user, without relaxing their focus, gradually moves their finger from a position immediately above the second post to a position directly above the first post while remaining cognizant at all times of the visual biofeedback, without focusing on it. If the user focuses on the visual biofeedback it will disappear, because it only exists while the visual system is focused binocularly on their index finger through its travel. This exercise is repeated for 5–10 minutes. After completing the exercises the user is likely to experience some discomfort (eyestrain) due to exerting the musculature of the visual system. To relieve this temporary discomfort the user should place a sterile cloth moistened with cool water over their eyes for a few minutes. The old body building adage, "No pain no gain," applies to exercising the visual system too.

Initially, some individuals may not be able to keep their visual system in focus for more than a few minutes. This is because after when their eye muscles get fatigued they will immediately move to the resting distance of the individuals visual system. As a result of practice, the user will gradually be able to perform the exercises for increasingly longer periods of time. Eventually, they will be able to focus their eyes throughout the entire range of image planes defined by the personal binocular trainer with little or no effort, at the reading distance. Ultimately they will be able to focus their eyes throughout the entire range of image planes defined by the personal binocular trainer with little or no effort without the assistance of their index finger.

Remaining cognizant of the visual biofeedback during the exercises is crucial to their effectiveness, because it is proof that the individuals visual system is focused binocularly and functioning in accordance with Hering's Law of Equal and Symmetrical Eye Movements. If the visual biofeedback is not symmetrical it means that the individual's eyes are not focused binocularly.

The personal Binocular Trainer was not designed for use by unsupervised children. It should not be used by unsupervised children.

Operative Theory of Comprehension Enhancement—the Premises

The first premise of my theory is, reading is an unnatural behavior.

The second premise is that each of us has a certain amount of physiological effort, x, that we can use to influence the status of our visual system, and that this quantity, x, is subject to change.

The third premise is when we read, we each allocate some our physiological effort, to keep our visual system in focus and the balance of this physiological effort is allocated to developing an understanding of the semantic meaning of the material that we are reading.

The fourth premise is when we read we are continually engaged in a zero sum game. We have a certain amount of physiological effort that we can allocate. The most effort any of us can allocate is 100 percent. If we allocate 80 percent of our physiological effort on keeping our visual system in focus, the most that we can expend on comprehension is 20 percent. Inversely, if we allocate 20 percent of our physiological effort to keep our visual system in focus, we have 80 percent to allocate to developing an understanding of what we are reading (comprehension). As a general rule the more fatigued we are visually, the more effort we have to expend to keep the visual system focused and the less effort we can allocate to comprehension.

The fifth premise is the individuals with the greatest comprehension and longest attention spans expend the least amount of effort to keep their visual system in focus. [This is one reason why people who are successful in education typically wear glasses to correct for nearsightedness, their visual systems are locked at near (at rest), and they the effort they allocate to keeping in focus at near is negligible (2 percent) so they are allocating almost all of their effort to developing an understanding of the subject matter (98 percent)]. Conversely, individuals who spend excessive amounts of effort to keep their visual system in focus, will demonstrate extremely poor reading comprehension, and will manifest very specific physiological symptoms. For example they will continually lose their place on the page while reading and/or skip lines due to focusing, de-focusing and subsequently re-focusing at a different place than where they unconsciously lost their focus. After reading for an extended period of time they will experience eye (muscle) strain. Eye strain is an extremely unpleasant burning sensation.

The sixth premise is the amount of physiological effort required to keep the visual system in focus can be reduced. A decrease in the amount of effort required to maintain binocular focus, automatically increases the amount of physiological effort that can be allocated to developing an understanding of the semantic meaning of the material that is being read. I hypothesize that re-allocating this effort will yield a measurable increase in reading comprehension.

The seventh premise is the sixth premise can be realized through the use of the personal Binocular Trainer.

I claim:

1. A hand held device for testing, exercising and recalibrating the musculature of the human visual system thereby enhancing binocular vision comprising:

(a) a horizontal shaft having two ends, (b) a first post affixed to one end of said horizontal shaft, (c) a second post is affixed to the other end of said horizontal shaft, said first post and said second post are oriented vertically in the same plane, said second post is positioned a linear distance from said first post; and (d) means for aligning said first post and said second post in the same vertical plane.

2. The device of claim 1, wherein said first post presents a different color or pigmentation which distinguishes it from said second post.

3. The device of claim 1, wherein said horizontal shaft is supported by a handle and said handle is positioned a linear distance from the center of said horizontal shaft.

* * * * *